(12) United States Patent
Roman et al.

(10) Patent No.: US 6,685,707 B2
(45) Date of Patent: Feb. 3, 2004

(54) CRANIAL CLAMP AND METHOD FOR FIXATING A BONE PLATE

(75) Inventors: Shawn David Roman, Orange Park, FL (US); Richard Champion Davis, III, Hollywood, FL (US); Jeffrey Allen Duncan, Jacksonville, FL (US); Derek Sean Lewis, Jacksonville, FL (US); Kevin T. Stone, Winona Lake, IN (US)

(73) Assignee: Walter Lorenz Surgical, Inc., Jacksonville, FL (US)

( * ) Notice: Subject to any disclaimer, the term of this patent is extended or adjusted under 35 U.S.C. 154(b) by 0 days.

(21) Appl. No.: 10/255,146

(22) Filed: Sep. 25, 2002

(65) Prior Publication Data

US 2003/0125743 A1 Jul. 3, 2003

Related U.S. Application Data

(60) Provisional application No. 60/324,658, filed on Sep. 25, 2001.

(51) Int. Cl.[7] .............................................. A61B 17/84
(52) U.S. Cl. .......................... 606/72; 606/73; 606/213
(58) Field of Search .............................. 606/60, 69–73, 606/75, 151, 213, 215, 216, 232; 411/155, 156, 338, 339, 525, 526, 527, 544

(56) References Cited

U.S. PATENT DOCUMENTS

| 276,135 A | 4/1883 | Cooley |
|---|---|---|
| 741,747 A | 10/1903 | Walz |
| 1,105,105 A | 7/1914 | Sherman |
| 1,390,485 A | 9/1921 | Bell |
| 1,510,416 A | 9/1924 | Pietz et al. |
| 1,616,232 A | 2/1927 | Roberts et al. |
| 2,077,804 A | 4/1937 | Morrison |
| 2,238,238 A | 4/1941 | Westrope |
| 2,329,471 A | 9/1943 | King |
| 2,489,870 A | 11/1949 | Dzus |

(List continued on next page.)

FOREIGN PATENT DOCUMENTS

| DE | 1 089 116 | 9/1960 |
|---|---|---|
| DE | 2 125 556 | 6/1972 |
| DE | 28 06 609 B1 | 7/1979 |

(List continued on next page.)

OTHER PUBLICATIONS

Codman & Shurtleff, Inc., Neurosurgical Quality Instruments, Copyright, 1965, pp. 10–13.
For The Few Who Know The Difference, TiMesh, Inc. (1 sheet).
"Internal Fixation of Small Fractures," Technique Recommended by the AAO–ASIF Group, U. Heim & K.M. Pfeiffer, copyright Springer—Verlag, Berlin–Heidelberg, 1974, 1982 & 1988.

(List continued on next page.)

*Primary Examiner*—David O. Reip
(74) *Attorney, Agent, or Firm*—Harness, Dickey & Pierce, P.L.C.

(57) ABSTRACT

A clamp assembly for repairing a bone defect according to the invention includes a base, a cap opposing the base, and a post connecting the cap and the base in a fastening position on adjacent bone plate and surrounding cranium. The clamp assembly may further include an applier interacting with the post to position the cap and base in the fastening position. A method according to the invention includes placing the base and cap on opposing internal and external surfaces of the bone plate, with a portion of each of the base and cap overlapping a border of junction between the bone plate and surrounding bone. The post is rotated to bring the base and cap to the fastening position. The method may further include removing a distal portion of the post projecting from the cap and leaving a proximal portion of the post projecting from the cap and which can be deformed to secure the base and cap in the fastening position.

29 Claims, 7 Drawing Sheets

U.S. PATENT DOCUMENTS

| | | |
|---|---|---|
| 2,494,229 A | 1/1950 | Collison |
| 2,511,051 A | 6/1950 | Dzus |
| 2,576,649 A | 11/1951 | Slind |
| 2,791,868 A | 5/1957 | Viken |
| 2,846,744 A | 8/1958 | Becker |
| 3,019,887 A | 2/1962 | Lowden |
| 3,281,171 A | 10/1966 | Hughes |
| 3,547,114 A | 12/1970 | Haboush |
| 3,712,357 A | 1/1973 | Corbett et al. |
| 3,741,205 A | 6/1973 | Markolf et al. |
| 3,779,240 A | 12/1973 | Kondon |
| 3,790,507 A | 2/1974 | Hodosh |
| 3,875,936 A | 4/1975 | Volz |
| 4,033,243 A | 7/1977 | Kirrish et al. |
| 4,116,200 A | 9/1978 | Braun et al. |
| 4,219,015 A | 8/1980 | Steinemann |
| 4,245,545 A | 1/1981 | Freeman |
| 4,275,490 A | 6/1981 | Bivins |
| 4,360,025 A | 11/1982 | Edwards |
| 4,503,848 A | 3/1985 | Caspar et al. |
| 4,643,610 A | 2/1987 | Bien |
| 4,651,724 A | 3/1987 | Berentey et al. |
| 4,669,473 A | 6/1987 | Richards et al. |
| 4,683,878 A | 8/1987 | Carter |
| 4,688,561 A | 8/1987 | Reese |
| 4,793,335 A | 12/1988 | Frey et al. |
| 4,802,477 A | 2/1989 | Gabbay |
| 4,875,815 A | 10/1989 | Phillips, II |
| 4,903,691 A | 2/1990 | Heinl |
| 4,905,679 A | 3/1990 | Morgan |
| 4,905,680 A | 3/1990 | Tunc |
| 4,923,471 A | 5/1990 | Morgan |
| 4,988,351 A | 1/1991 | Paulos et al. |
| 5,013,316 A | 5/1991 | Goble et al. |
| 5,087,202 A | 2/1992 | Krenkel |
| 5,098,433 A | 3/1992 | Freedland |
| 5,139,497 A | 8/1992 | Tilghman et al. |
| 5,167,665 A | 12/1992 | McKinney |
| 5,196,016 A | 3/1993 | Buser et al. |
| 5,201,737 A | 4/1993 | Leibinger et al. |
| 5,250,049 A | 10/1993 | Michael |
| 5,268,001 A | 12/1993 | Nicholson et al. |
| 5,269,784 A | 12/1993 | Mast |
| 5,342,393 A | 8/1994 | Stack |
| 5,346,492 A | 9/1994 | Morgan |
| 5,350,399 A | 9/1994 | Erlebacher et al. |
| 5,352,229 A | 10/1994 | Goble et al. |
| 5,372,598 A | 12/1994 | Luhr et al. |
| 5,433,053 A | 7/1995 | Tulloch |
| 5,433,719 A | 7/1995 | Pennig |
| 5,468,242 A | 11/1995 | Reisberg |
| 5,501,685 A | 3/1996 | Spetzler |
| 5,549,620 A | 8/1996 | Bremer |
| 5,578,036 A | 11/1996 | Stone et al. |
| 5,601,558 A | 2/1997 | Torrie et al. |
| 5,669,912 A | 9/1997 | Spetzler |
| 5,707,373 A | 1/1998 | Sevrain et al. |
| 5,722,976 A | 3/1998 | Brown |
| 5,741,282 A | 4/1998 | Anspach, III et al. |
| 5,800,436 A | 9/1998 | Lerch |
| 5,916,200 A | 6/1999 | Eppley et al. |
| 5,928,244 A | 7/1999 | Tovey et al. |
| 6,068,631 A | 5/2000 | Lerch |

FOREIGN PATENT DOCUMENTS

| | | |
|---|---|---|
| DE | 296 14 920 U1 | 10/1996 |
| DE | 296 14 921 U1 | 10/1996 |
| DE | 296 14 922 U1 | 10/1996 |
| DE | 296 14 923 U1 | 10/1996 |
| DE | 196 03 887 A1 | 8/1997 |
| EP | 0 290 138 A2 | 4/1987 |
| EP | 0 291 632 A1 | 5/1987 |
| EP | 0 433 852 A1 | 6/1991 |
| EP | 0 510 390 A1 | 10/1992 |
| FR | 2 386 301 | 11/1978 |
| FR | 2 631 539 A1 | 5/1988 |
| JP | H05-21954 | 3/1993 |
| JP | H05-220714 | 8/1993 |
| SU | 1512584 A1 | 10/1989 |
| SU | 1600713 | 10/1990 |
| SU | 1655477 A1 | 6/1991 |
| WO | PCT/US97/01398 | 2/1997 |
| WO | 97/29708 | 8/1997 |

OTHER PUBLICATIONS

"Manual of Internal Fixation Technique," Recommended by the AO–Group, M.E. Mueller, M. Allgower & H. Willenegger, copyright Springer–Verlag, Berlin–Heidelberg, 1970.

Four pages from catalog of products offered by Codman & Shurtleff, undated, disclosing Burr Hole Buttons.

Translation of G 85 23 003.8 (Germany), Bone Plate, Feb. 1986, Oswald Leibinger Gmbh (Owner).

Hans G. Luhr, M.D., D.M.D., "Indications of Use of a Microsystem for Internal Fixation in Craniofacial Surgery," J. of Craniofacial Surgery, vol. 1, No. 1, Jan., 1990, pp. 35–52.

Howmedica International, Inc., "Vitallium–Verschiedene Implantate," p. 54.

Leibinger LP, "Leibinger," copyright 1995 (1 sheet).

Walter Lorenz Surgical, Inc., "Surgical Instrument Catalog 5th Edition," copyright 1993, pp. 10–11.

Walter Lorenz Surgical, Inc., 1.5/2.0mm Combination Titanium Osteosynthesis System. copyright 1994.

Aesculap CranioFIX brochure, dated Mar. 1998, (9 sheets), along with sixteen (16) sheets of color photographs of the corresponding instruments, set forth in the brochure.

Aesculap CranioFIX Titanium Clamp Instruction Manual (28 sheets) in various languages, dated Jan. 1999, along with one (1) color photograph of an Aesculap CranioFIX Titanium Clamp.

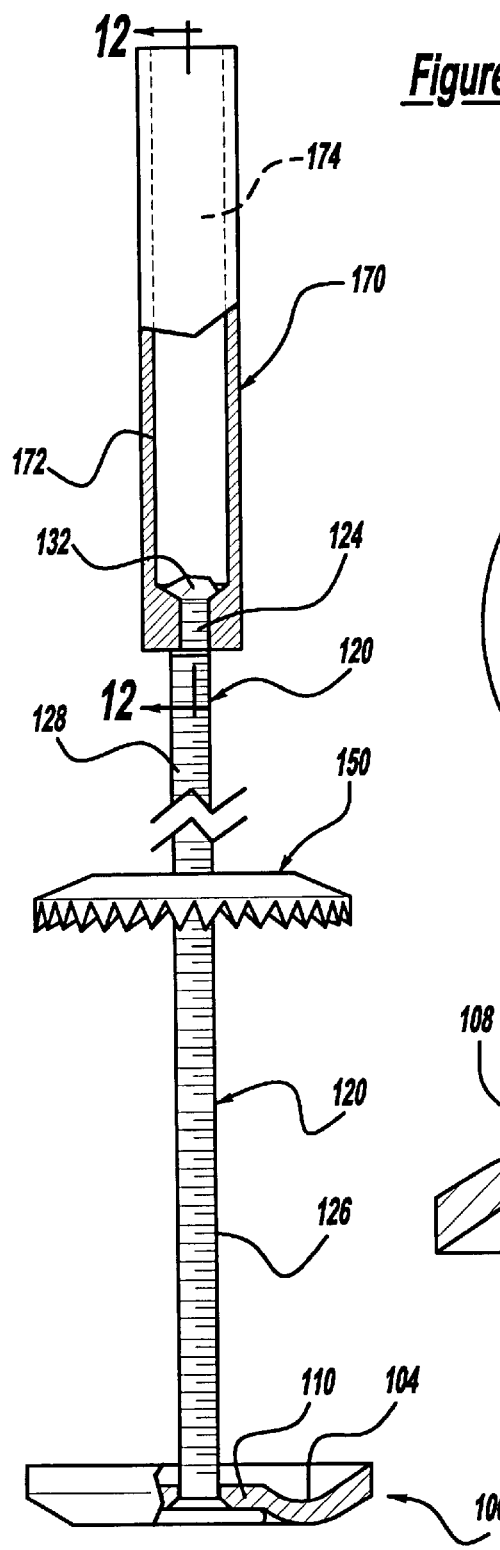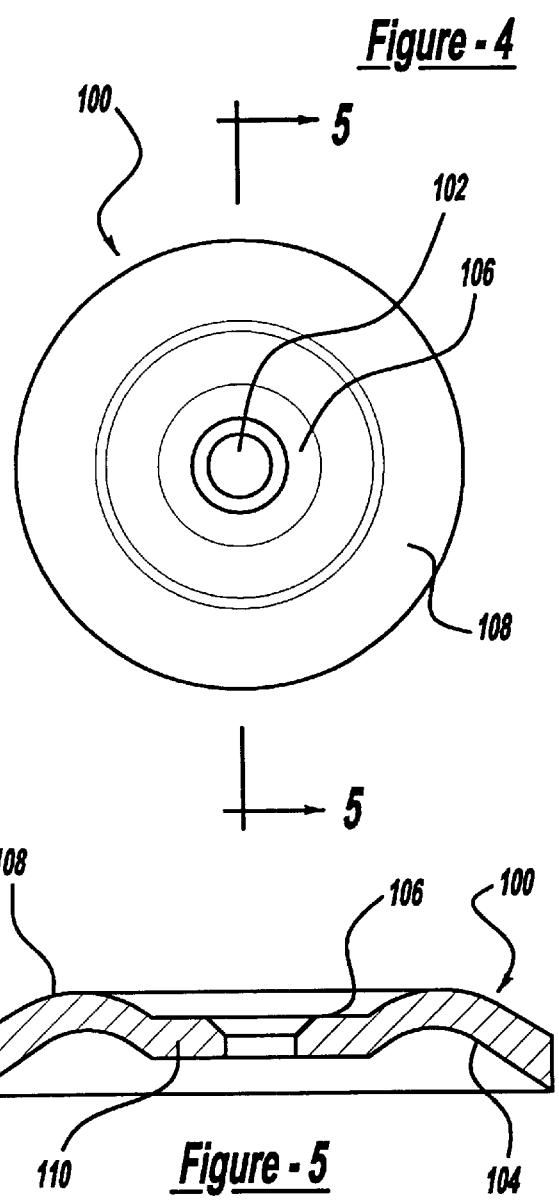
Figure - 3
Figure - 4
Figure - 5

CRANIAL CLAMP AND METHOD FOR FIXATING A BONE PLATE

CROSS-REFERENCE TO RELATED APPLICATIONS

This case claims priority from U.S. provisional patent application Ser. No. 60/324,658, filed Sep. 25, 2001.

FIELD OF THE INVENTION

This invention relates to a fastener for quickly and securely fastening a bone plate to surrounding bone. In one embodiment, the fastener contains a torque-limiting feature to prevent over tightening when in the fastening position. In another embodiment, the invention relates to an instrument for applying the fastener to a bone plate and surrounding bone.

BACKGROUND AND SUMMARY OF THE INVENTION

When performing surgery on the brain, it is often necessary to perform a craniotomy to provide access to portions of the brain. A craniotomy is a surgical procedure in which a portion of the cranium is removed to permit access to the brain. To perform the craniotomy, one or more holes are initially drilled through the skull. These holes, known as "burr holes," may be located, for example, at the corners of a triangular region of bone that is to be temporarily removed. A saw, i.e., a craniotome, is then used to cut the skull along the line of separation connecting the adjoining burr holes. The resulting bone cover or bone plug is subsequently lifted from the underlying dura matter to expose the brain. The bone cover may either be completely removed from the cranium, or folded back in a flap along an uncut edge of the flap.

After completion of the procedure on the brain, the bone cover must be re-attached to the skull. Several devices have been developed that are used to facilitate securing the bone cover to the skull. These devices suffer from the disadvantage that they are cumbersome or inefficient to apply to the bone flap and surrounding bone. Further, prior designs are relatively rigid, thus decreasing conformance to the curvature of the skull. Moreover, prior designs often required significant instrumentation to apply and/or adjust the device used to secure the bone cover to the skull. Finally, prior designs may require removal of the fastening device after sufficient healing along the line of separation.

The Cranial Clamp And Method For Fixating A Bone Plate according to the invention generally includes a cap and base adjustably joined by a post for threadably bringing the opposing cap and base closer together, thereby tightening them against the internal and external surfaces of the bone plate and surrounding cranium. The base and cap securely fix the bone plate to the surrounding bone. In one embodiment, at least one of the base, cap and post include resorbable material.

The clamp according to the invention may further include an applier interacting with the post to position the cap and base to securely fix the bone plate to the surrounding bone. Once appropriately secured, the applier is removed from the post while leaving the cap and base interconnected. In one embodiment, the applier includes a keyed bore and the post includes a key for engaging the keyed bore of the applier.

The clamp according to the invention may also include a torque-limiting feature on the post. The torque-limiting feature prevents stripping of the threaded interconnection between the post and cap or overtightening of the cap relative the base. In one embodiment, the torque-limiting feature is disposed at a junction between an elongated body portion and a keyed portion of the post.

The method for fixating a bone plate in a bony defect according to the invention allows a bone plate to be fixed in apposition against a transverse face of surrounding bone along the border of junction between the bone plate and surrounding bone. A base connected to an elongated externally threaded post projecting from the base, and a cap with an internally threaded collar for mating and threaded engagement with the threaded post connected to the base, is provided. In one embodiment, at least one of the base, cap, and post include resorbable material. The base and cap are placed on opposing internal and external surfaces of the bone plate, with a portion of each of the base and cap overlapping the border of junction. The post is rotated into the collar to bring the base and cap to a fastening position having the base and cap in tight engagement against the opposing internal and external surfaces of the bone plate. At least one of the base, cap, and post include resorbable material, which is resorbed by the body.

The method according to the invention may further include providing an applier, wherein the applier rotates the post through inter-engagement of the applier with the post. The method according to the invention may also include removing a distal portion of the post projecting from the cap and leaving a proximal portion of the post projecting from the cap. Moreover, the proximal portion of the post projecting from the cap may be deformed to secure the base and cap in the fastening position.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 3 is a partially sectioned side view of an assembled clamp and applier according to the invention;

FIG. 4 is a top view of a base of a clamp according to the invention;

FIG. 5 is a sectional view cut along line 5—5 of FIG. 4;

DETAILED DESCRIPTION OF THE PREFERRED EMBODIMENTS

Figure 1:
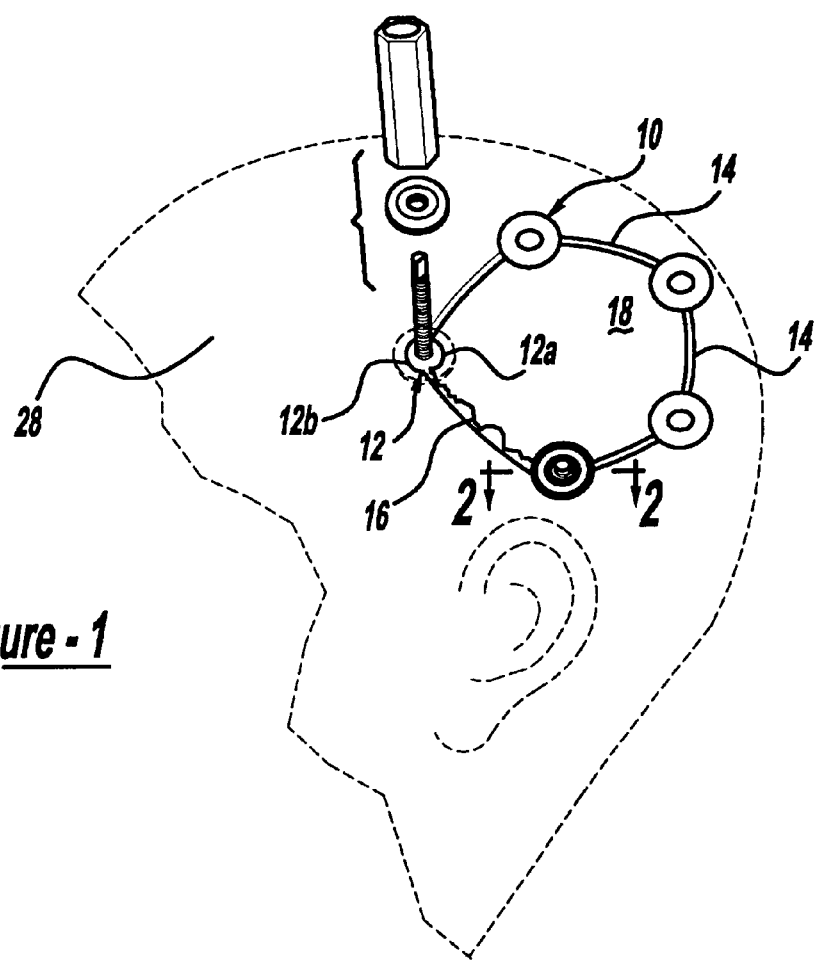
FIG. 1 is a partial perspective view of a clamp and applier according to the invention securing a bone plate to surrounding cranium.

The following description of the preferred embodiment(s) is merely exemplary in nature and is in no way intended to limit the invention, its application, or uses. While the present invention is shown securing a bone plate to a surrounding cranium, the fastener of the present invention may be used in other surgical and non-surgical applications as well.

The present invention includes fasteners for securing flat or curved plate structures to each other. The invention also includes a positioning and applying instrument that is particularly useful for positioning and applying the fasteners in a surgical wound and for securing the fasteners to each other.

As shown in the drawings, the fastener according to the invention is a clamp 10 for closing a craniotomy. A craniotomy is performed by incising pericranium and muscle with cutting diathermy in the line of an intended bone flap. An incision is not made interiorly where a pedicle of pericranium or temporalis muscle is often left uncut to allow some blood supply to the bone and overlying tissue to remain intact. Alternatively, the pericranium and muscle may be detached completely from the intended bone flap.

Figure 2:
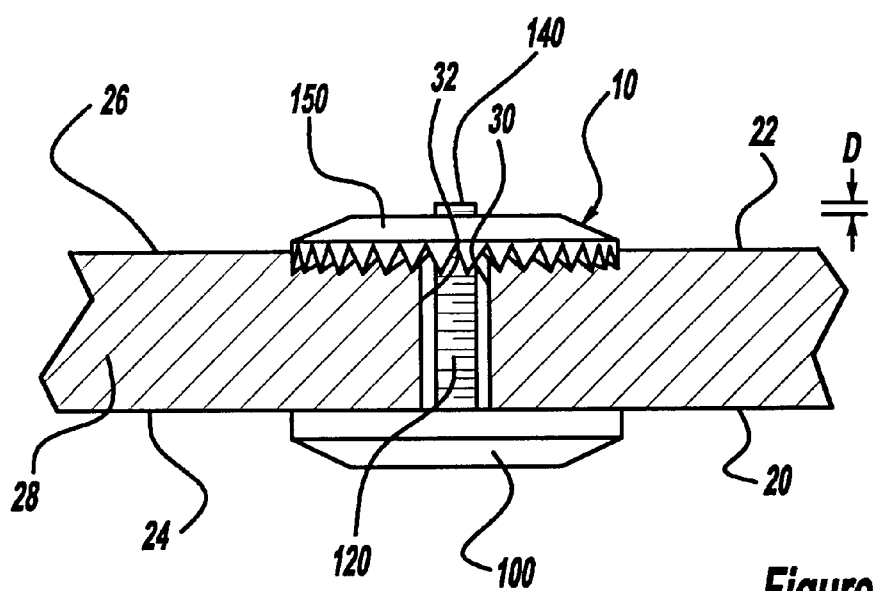
FIG. 2 is a partial sectional view of a clamp and applier cut along line 2—2 of FIG. 1.

As illustrated in FIGS. 1 and 2, the craniotomy is performed by making a series of burr holes 12 through the cranium 28 about six or seven centimeters apart with a cranial perforator. Alternatively, a trephine can be used. The underlying dura matter is separated from the bone covering the osteotomy site ("the bone cover") using a periosteal elevator. Osteotomies 14 between the burr holes 12 are then made using a craniotome that is passed between adjacent burr holes 12 and moved back and forth to make the osteotomies 14 from the internal to the external surfaces of the cranium 28. Alternatively, a Gigli flexible saw can be used to make the osteotomies 14. A base 16 is not cut with the saw. A bone forceps (such as a deVilbis forceps) is used to ply a bone plate 18 until the bridge breaks at the base 16 when the bone plate 18 is elevated.

The bone plate 18 is separated from the surrounding cranium 12 and 28 along a line of separation formed by osteotomies 14. Each burr hole 12 has a plate portion 12(a) and a complimentary cranial portion 12(b), which together form the completed burr hole 12. Trephines come in graduated sizes, for example, between 0.5 and 2 inches (13–51 millimeters) diameter for drilling burr holes 12 of sizes varying across this usual range.

The bone plate 18 may be completely removed if osteotomies connect all of the burr holes 12. It is often preferred, however, to leave an intact edge of the craniotomy (such as base 16) to preserve the blood supplied to the bone. In either case, the bone plate 18 is typically referred to as the cranial cover.

After the neurosurgical procedure is performed, the bone defect must be repaired by placing the bone plate 18 back in the defect with opposing internal surface 20 and external surface 22 substantially coplanar or aligned with the internal surface 24 and external surface 26 of surrounding cranium 28. A transverse face 30 of bone plate 18 must also be fixed in opposition with a transverse face 32 of cranium 28 along a border of junction defined by the osteotomy 14 between bone plate 18 and surrounding cranium 28.

In an embodiment shown in FIG. 3, the clamp 10 includes a first member or base 100 selectively connected to a second member or cap 150 via a post 120. The cap 150 and base 120 are brought toward one another by an instrument or applier 170. In one embodiment, the base 100, post 120, cap 150 and applier 170 are assembled prior to use in securing the bone plate 18. In another embodiment, the base 100, post 120 and cap 150 are assembled prior to use in securing the bone plate 18. Yet another embodiment include an assembled base 100 and post 120, and the cap 150 and applier 170 are assembled after positioning the base 100 and post 120 to secure the bone plate 18.

As shown in FIGS. 4 and 5, the base 100 is formed by a generally solid disk having a central aperture 102, an annular inner face 104 surrounding the aperture 102, and an outer face 108 except for a central recess 106 disposed coaxial with the aperture 102. The outer face 108 surrounds the central recess 106 and generally accommodates the annular inner face 104. The inner face 104 and outer face 108 circumscribe a collar 110 projecting inwardly from the inner face 104 coaxially about central aperture 102. In this embodiment, aperture 102 extends through base 100 and is adapted to receive the post 120, whereby the post 120 is able to rotate relative the base 100. In other embodiments, aperture 102 may only have an opening at the inner side of collar 110 and not extend through the base 100.

Figure 6:
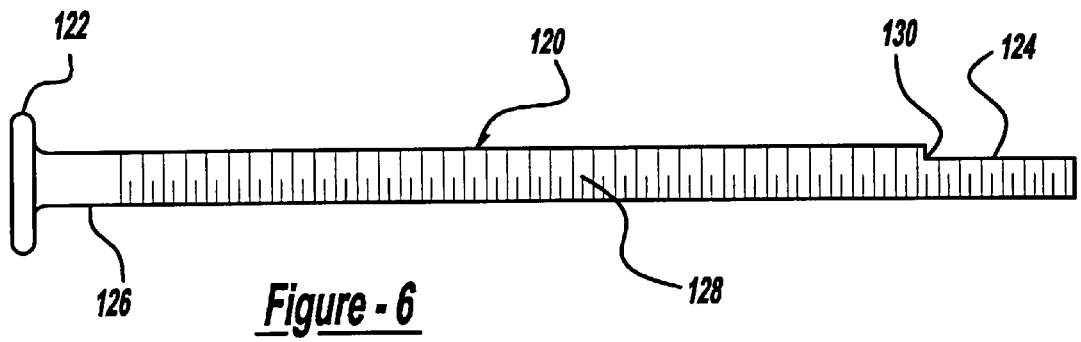
FIG. 6 is a side view of a post of the clamp according to the invention.
Figure 7:
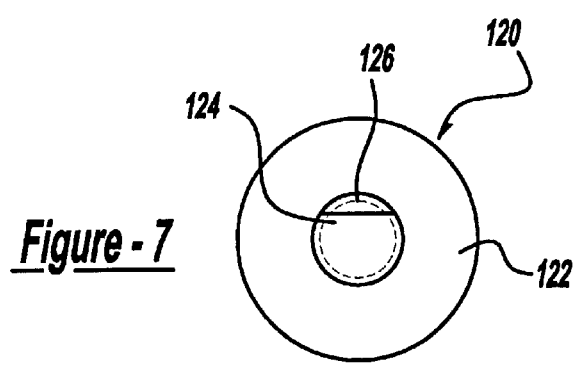
FIG. 7 is an end view of the post of FIG. 6.
Figure 8:
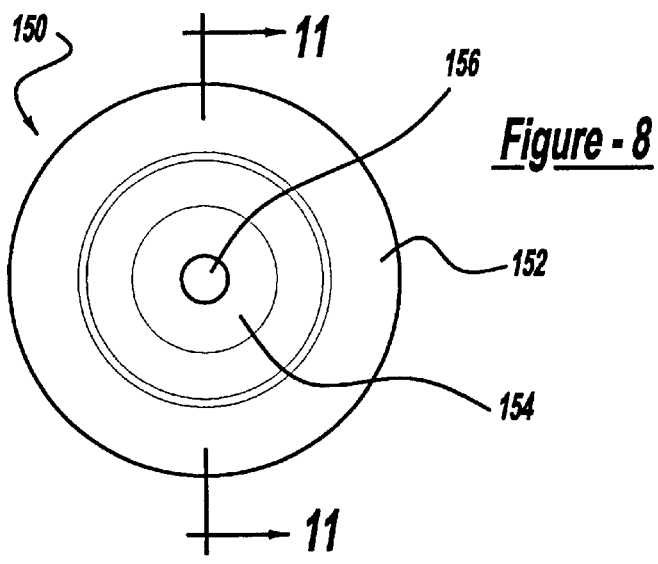
FIG. 8 is a top view of a cap of the clamp according to the invention.
Figure 9:
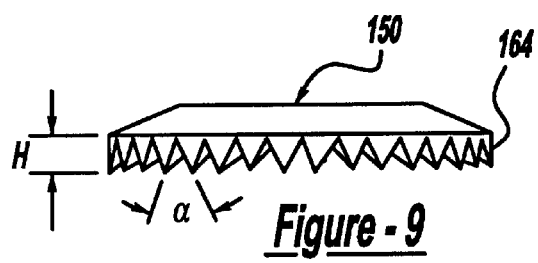
FIG. 9 is a side view of the cap of FIG. 8.
Figure 10:
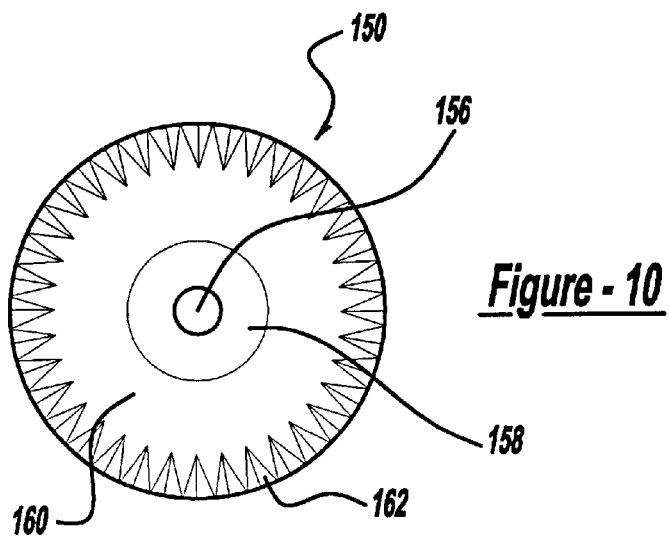
FIG. 10 is a bottom view of the cap of FIG. 8.
Figure 11:
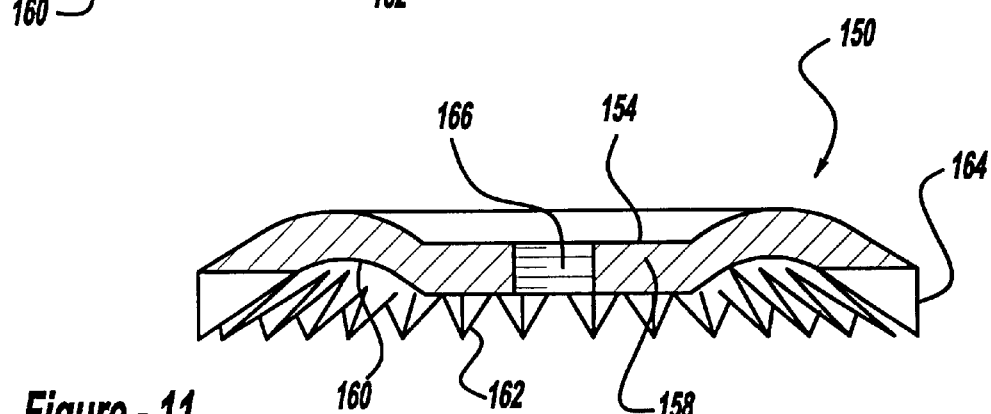
FIG. 11 is a sectional view cut along line 11—11 of FIG. 8.
Figure 12:
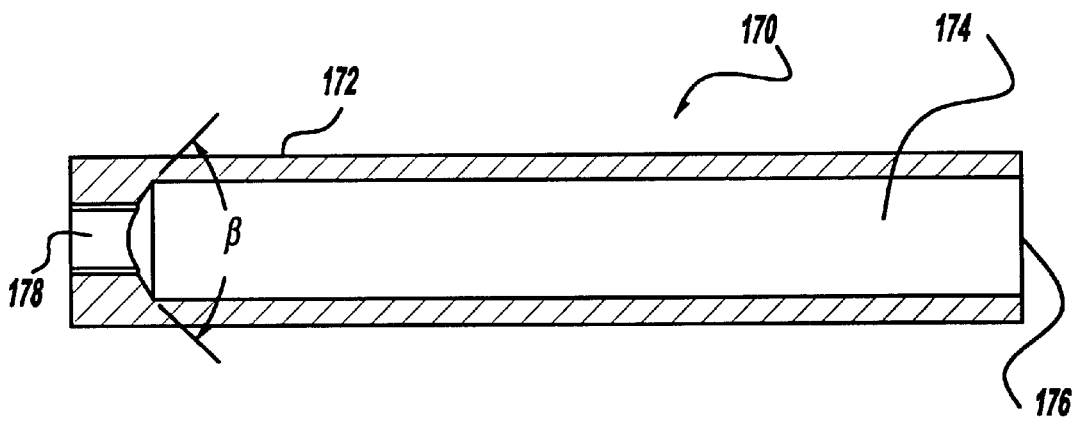
FIG. 12 is a sectional view of an applier according to the invention cut along line 12—12 of FIG. 3.
Figure 13:
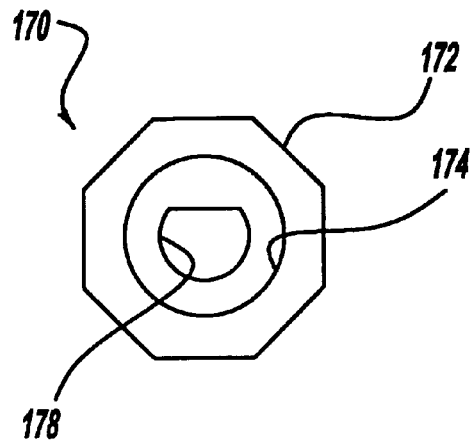
FIG. 13 is an end view of the applier of FIG. 12.

As shown in FIGS. 6 and 7, the post 120 includes a head 122 at a first end and a key 124 at a second end. A substantially cylindrical, elongated body 126 extends between the head 122 and key 124, and generally includes ribs or threads 128 along its length. Threads 128 will be used in the following description, but ribs are within the scope of the invention. At the head end of the post 120, the threads 128 taper or run out from a minor to major diameter of the body 126 over 360 to 720 degree revolutions. In one embodiment, the junction of the body 126 and key 124 provides a torque-limiting feature 130 to allow the key 124 to break from the body 126 to prevent stripping the threaded interface between the post 120 and cap 150 or over-tightening the clamp 10. In one embodiment, the ribs or threads 128 along post 120 are pliable and resilient due to material elasticity. Such pliable, resilient ribs or threads 128 allow the cap 150 to be quickly secured by ratcheting cap 150 along the threads 128 on the post 150 to quickly position the cap 150 relative the base 100 along post 120. Due to the elasticity in engagement of the ribs or threads, however, once the cap 150 is ratcheted in position along post 120, it can be further adjusted toward base 100 by threaded rotation or further ratcheting. Further, in one embodiment, threads 128 can extend partially along the elongated body 126 of the post 120. In this manner, the cap 150 can be slid along a portion of the elongated body 126, which may include ribs, prior to engaging the threads 128.

The head 122 is preferably a rounded disk shape disposed coaxially with the elongated body 126, which flares outwardly at the junction with the head 122. In one embodiment, the key 124 is a generally D-shaped cross section formed at the second end of the post 120. In other embodiments, the shape or cross section of the key 124 may differ. When clamp 10 is assembled for use, the post 126 is received coaxially through the aperture 102 of the base 100 such that head 122 seats in the central recess 106, as best shown in FIG. 3.

The cap 150 fastens to the base 100 to secure the bone plate 18 in place and occlude the burr holes 12. As shown in FIGS. 6–9, the cap 150 is a generally solid disk with an outer face 152 except for a central recess 154 disposed coaxially about a central aperture 156 extending therethrough. The cap 150 has an annular inner face 160 including a collar 158 surrounding the aperture 156. The inner face 160 comprises an arcuate channel coaxially surrounding the collar 158 and aperture 156. Further, the inner face 160 includes a series of radial teeth 162 radiating circumferentially toward the outer diameter of the inner face 160. The teeth 162 form a serrated edge 164 about the periphery of cap 150. The teeth 162 are disposed at an angle I and height H along the serrated edge 164. For example, in an approximately 14 millimeter cap 150, the teeth 162 are separated by an angle I approximating 53 degrees at a height H approximating 0.047 inches. In the embodiment shown, the aperture 156 of collar 158 includes internal threads 166. For this embodiment, the threads are left-handed, but should compliment the threads 128 of the post 120 in other embodiments.

As shown in FIGS. 1, 3, 12 and 13, the applier 170 is used to position and fasten the clamp 10. The applier 170 includes a generally hexagonal elongated body 172 including a bore 174 extending generally coaxially therethrough along its length. At a first end, the bore 174 extends to an opening 176. At an opposite end, the bore 174 extends to a keyed bore 178. In one embodiment, keyed bore 178 has a generally D-shaped cross section to compliment the cross section of key 124. When key 124 is inserted into keyed bore 178, rotation of body 172 rotates the post 120. In one embodiment, the applier 170 is secured to the post 120 prior to use in securing a bone plate 18 by deforming a portion of the post 120 extending through the keyed bore 178 and into the bore 174. This deformation, indicated as 132 in the drawings, secures the post 120 and applier 170 to one another. As shown, the body 172 of the applier has a generally hexagonal cross section, but in other embodiments can have other shapes and cross sections. Further, bore 174 tapers to keyed bore 178 at an angle θ. In this embodiment, angle θ approximates 118 degrees. Also in this embodiment, bore 174 extends approximately 90 percent of the length of applier 170, while keyed bore 178 extends approximately ten percent thereof.

In one embodiment, clamp 10 includes resorbable materials. In one variation of this embodiment, the base 100, post 120, and cap 150 are all comprised of resorbable materials. In another variation, the base 100 and cap 150 are comprised of resorbable material, while the post 120 is comprised of a suitable biocompatible material. In yet another variation, either the base 100 or cap 150 is comprised of resorbable material, and the post 120 may be comprised of resorbable and/or biocompatible material. Alternatively, only the post 120 comprises resorbable material. The main benefit of using resorbable material is that the clamp 10, or components thereof, will resorb into the body over a generally predictable time period once a sufficient level of healing has occurred, for example, at the junction of a bone fracture, thus negating need for subsequent removal of the clamp 10.

One resorbable material is used in products marketed by Biomet, Inc. (Warsaw, Ind.) under the trademark LACTOSORB®. LACTOSORB® is an absorbable co-polymer synthesized from all natural ingredients: 82 percent L-lactic acid and 18 percent glycolic acid. Unlike the homopolymers in common use, such as 100 percent poly-L-lactic acid (PLLA) or 100 percent poly-glycolic acid (PGA), LACTOSORB® co-polymer is substantially amorphous (i.e., without crystallinity), meaning that its degradation is uniform, precluding the crystalline release most often associated with degrading homopolymers that have been associated with inflammatory reactions. Furthermore, the LACTOSORB® co-polymer ratio permits the polymer to retain most of its strength for six to eight weeks, which is appropriate for healing, but not so long as to raise concerns about long-term stress shielding. It should also be understood that any other type of resorbable material may also be used herein.

In an alternate embodiment, the clamp 10 includes of non-resorbable, biocompatible materials. In one variation of this embodiment, the base 100, post 120 and cap 150 are all comprised of non-resorbable, biocompatible materials. In another variation, the base 100 and cap 150 are comprised of resorbable material, while the post 120 is comprised of a suitable non-resorbable, biocompatible material. In yet another embodiment, either the base 100 or cap 150 is comprised of resorbable material, while the other of the base 100 and cap 150 and the post 120 may be comprised of a suitable non-resorbable, biocompatible material. Alternatively, both the base 100 and cap 150 comprise non-resorbable, biocompatible material and the post 120 comprises resorbable material.

One non-resorbable, biocompatible material is titanium. Titanium and its alloys are high strength, durable and corrosion resistant materials. A titanium containing alloy such as, for example, $Ti_6Al_4V$ is commonly used in surgical applications. $Ti_6Al_4V$ is inert to human body fluids thus its resistance in bodies is very high. Furthermore, $Ti_6Al_4V$ has been shown to have a high resistance to abrasion and also has a high fatigue resistance. It should be understood that any other suitable type of non-resorbable, biocompatible material may also be used herein and should be considered within the scope of the present invention, including other metals having a layer of biocompatible cement to line the metal in order to prevent the body's immune system from rejecting the implanted material.

The clamp 10 according to the invention can be assembled in various ways for use in replacing the bone plate 18 following a craniotomy. For example, the clamp 10 can be provided unassembled for use in securing the bone plate 18, in which case a user would begin assembly of clamp 10 by inserting the post 120 into the base 10. In another embodiment, the clamp 10 may be provided to the user at least partially assembled, for example with the post 120 assembled to the base 100, or otherwise affixed thereto. In another embodiment, the clamp 10 would be assembled further by not only assembling the post 120 and base 100 to one another, but also connecting the post 120 to the cap 150. In this way, once the clamp 10 is in position to secure a bone plate 18, the applier 170 is connected to the post 120 for securing the bone plate 18 to the surrounding cranium 28. In yet another embodiment, the clamp 10 includes assembling the post 120 to the base 100 and cap 150, as well as securing the applier 170 to the post 120. The post 120 may be secured to the applier 170 in various ways; as shown, an end portion of the post 120 extending through the key shaped bore 178 and into the bore 174 is deformed after assembly of the post 120 to both the base 100 and cap 150, whereby the entire assembly of the base 100, post 120, cap 150, and applier 170 is provided assembled for use in replacing the bone plate 18 following the craniotomy.

The clamp 10 is used to replace the bone plate 18 following a craniotomy, as shown in FIG. 1. The craniotomy is performed by providing at least one craniotomy hole or multiple holes, such as burr holes 12, through the skull. The burr holes 12 are subsequently connected by osteotomies 14 to create a separation border for the bone plate 18, which may be a plate that is removed or a flap that is folded back along one edge. Alternatively, a circular bone plate 18 can be formed by providing one burr hole 12 and a circular osteotomy beginning and ending at the one burr hole 12. In each case, the craniotomy opening includes a portion 12a of at least one burr hole 12 formed in the bone plate 18 and a complimentary portion 12b of the hole formed in the surrounding cranium 28. The subsequent description employs the example of multiple burr holes 12 and osteotomies 14 connecting the holes 12, as shown in FIG. 1.

As shown in FIG. 2, the bone plate 18 has the internal surface 20 and external surface 22 respectively placed in substantially coplanar relationship with the internal surface 24 and external surface 26 of the surrounding cranium 28 when a craniotomy is closed. Opposing transverse faces 30, 32 of the bone plate 18 and surrounding cranium 28 appose along the separation border when the bone plate 18 is replaced. Faces 30, 32 are generally parallel to each other when in apposition.

In a method of the present invention, the bone plate 18 is folded back along a base 16 or completely removed to expose the underlying dura matter and brain. In one embodiment, following the intracranial procedure, and prior to replacing the bone plate 18 into its original orientation within the craniotomy opening, the assembled base 100 and post 120 is placed below each burr hole 12 with the inner face 104 of the base 100 against the internal surface 24 of the cranium 28 and the post 120 extending through the hole 12. The base 100 overlaps the margins of hole 12 and the separation border between the bone plate 18 and surrounding cranium 28. The collar 110 projects upwardly toward the hole 12 and the post 120 extends upwardly and through the hole 12. In another embodiment, the assembled base 100, post 120, and cap 150 are positioned with the inner face 104 and the base 100 against the internal surface 24 of the cranium 28, the post 120 extending through the hole 12, and the cap 150 positioned above the hole 12 with the inner face 160 of the cap 150 facing the external surface 26 of the cranium 28. In yet another embodiment, the applier 170 is connected to the keyed end 124 of the post 120 such that the assembled base 100, post 120, cap 150, and applier 170 are positioned relative each bore hole 12 with the inner face 104 of the base 100 against the internal surface 24 of the cranium 28, the post 120 extending through the hole 12, and the inner face 160 of the cap 150 facing the external surface 26 of the cranium 28. The bone plate 18 is then replaced into the craniotomy opening, for example, by folding the bone plate 18 along base 16 back down into the craniotomy opening.

After the bone plate 18 is restored to its original position in the craniotomy opening, complimentary portions 12a, 12b now reform hole 12. The post 120 is positioned within hole 12 with the inner face 104 of the base 100 engaging the internal surfaces 20 and 24 of bone plate 18 and cranium 28, respectively. If not already assembled to the post 120, the cap 150 is positioned over the reformed hole 12 to engage the post 120 above the hole 12. The post 120 is introduced into the collar 158 of cap 150 through the aperture 156. In one variation of this embodiment, wherein the threads 128 extend generally along the length of the elongated body 126 of the post 120, the threads of internally threaded collar 158 engage the threads 128 of externally threaded elongated body 126 and the cap 150 is threaded into engagement with bone plate 18 and surrounding cranium 28. In another variation of this embodiment, wherein a portion of the elongated body 126 is externally threaded, the cap 150 is slid along an unthreaded leading portion of the elongated body 126 until it engages an externally threaded portion of the elongated body 126. In any embodiment, the ribs or threads 128 may be pliable and resilient, whereby the cap 150 is ratcheted along the externally ribbed or threaded elongated body 126 into contact with the external surface of the cranium 28 and bone plate 18.

In one embodiment, once the cap 150 is in position to be threadably driven, the applier 170 is attached to the post 120 by inserting the key 124 of the post 120 into the keyed bore 178 of the applier 170. In another embodiment, the applier 170 is connected to the post 120 prior to positioning the post 120 on the burr hole 12. In each embodiment, the cap 150 is held in place with one hand while the applier 170 is rotated with the other hand, causing the post 120 to rotate relative the base 100 and threadedly engage the cap 150 to diminish the distance between the base 100 and the cap 150 and tighten respective inner faces 104, 160 of the base 100 and cap 150 against the respective internal and external surfaces of the cranium 28 and bone plate 18. The cap 150 and base 100 are brought together in frictional engagement against opposing faces of the bone plate 18 and surrounding cranium 28, thereby clamping the bone plate 18 and surrounding cranium 28 to each other. The teeth 162 of the cap 150 anchor the cap 150 to both the bone plate 18 and surrounding cranium 28, thereby preventing rotation of the cap 150 while the base 100 is secured thereto. The cap 150 is attached to the bone of the bone plate 18 and cranium 28 as the teeth 162 become progressively advanced into the bone by rotating the clamp 10.

The torque-limiting feature 130 disposed at the junction of the body 126 and key 124 of the post 120 allows the key 124 to break from the body 126 to prevent stripping the threaded interface of the post 120 and cap 150 or overtightening the cap 150 relative the base 100. The key 124 will separate from the body 126 of the post 120 before the threaded interface between the cap 150 and post 120 strips. In this manner, the time and expense of replacing a stripped clamp 10 is avoided, and a proper amount of frictional engagement of the cap 150 and base 100 against opposing faces of the bone plate 18 and surrounding cranium 28 is provided. The torque-limiting feature 130 of the post 120 could be provided in other ways within the scope of this invention, such as by notching the post 120 at a portion other than the junction of the key 124 and body 126, or narrowing the diameter of the post 120 at any point along the body 126 and key 124, among other ways.

After the cap 150 and base 100 are suitably brought together against the opposing faces of the bone plate 18 and surrounding cranium 28 to clamp the bone plate 18 and surrounding cranium 28 to each other, a distal portion of the post 120 is cut a distance D above the cap 150, as best shown in FIG. 2. The distance D is a distance suitable to provide a proximal portion 140 of the post 120 with enough material to secure the cap 150 to the post 120 upon deformation of the proximal portion 140 of post 120. In one embodiment, the distance D is approximately two millimeters for a 14 millimeter diameter cap 150. The remaining distance D of the post 120 is flattened or otherwise deformed to prevent the cap 150 from backing off the post 120 and away from the base 100. Preferably, opthalmic cautery or a heat pen is used to cut the post a distance D above the cap 150, and further used to deform the remaining distance D of the post 120 to secure the cap 150 relative the base 100, as best shown in FIG. 1. A heat pen, such as the LACTOSORB® Heat/Contouring Pen, is available from W. Lorenz Surgical of Jacksonville, Fla.

The clamp 10 is used to clamp the bone plate 18 to the surrounding cranium 28 at one or more of the burr holes 12, and preferably all of the burr holes 12 as shown in FIG. 1. The clamp 10 can also clamp the bone plate 18 to the surrounding cranium along an osteotomy 14. That is, use of the clamp 10 is not limited to occluding burr holes 12, but is useful for supporting a bone plate 18 in a circular or curved osteotomy 14 as well. A base 100 and post 120 is therefore positioned below each burr hole 12 or at discrete points along an osteotomy with the post 120 projecting up into and through the hole 12 on the line of separation prior to replacement of the bone plate 18. A cap 150 is then threaded along each externally threaded post 120 until the cap 150 and base 100 clamp the bone plate 18 and surrounding cranium 28 securely to each other. The cap 150 and base 100 are in a fixed relationship determined by the degree of advancement of the externally threaded post 120 into the internally threaded collar 158 of the cap 150, so that the movement of the bone plate 18 is substantially prevented. The bone plate 18 and surrounding cranium 28 are held firmly in place with respect to each other, which avoids inadvertent depression of the bone plate 18 and attendant catastrophic neurological consequences.

The outer face of the cap 150 diminishes the aesthetic problem of visible indentations on the skull or face overlying the craniotomy burr holes 12. Further, by employing a malleable material with high ductility for the cap 150, aesthetic problems are further reduced. The closed base 100 tightly engages the internal surfaces of the bone plate 18 and surrounding cranium providing ideal occlusion of the hole 12 to held avoid infection or trauma. The clamp 10 also clamps the bone plate 18 in place quickly, thereby diminishing the period of time the brain must be exposed and also reduces medical expenses associated with prolonged time in the operating room. In one embodiment, as explained previously, the clamp 10 is made partially or wholly of resorbable material so that the body can resorb the clamp after suitable bone growth across the osteotomies. Beside the biocompatibility of such materials, such a clamp 10 need not be removed by a follow-up neurosurgical procedure.

The clamp 10 may be made in many different sizes. For purposes of illustration, the diameter of the post 120 can be 1.8 millimeters (the same diameter as the apertures 156 and 102), the diameter of base 100 can be 14 millimeters, and the diameter of the cap 150 may be 14 millimeters. In one embodiment, the post 120 is 35.6 millimeters long, with key 124 extending approximately 5 millimeters from a leading end of the post 120.

The clamp 10 is adjustable for use in repairing craniotomies through bone of varying thickness. The pterion (in the temporal-parietal region), for example, is quite thin and would conventionally require a shorter fastener. Because the unused portion of the post 120 is simply removed once the base 100 and cap 150 are appropriately positioned, different-sized fasteners are not necessary. For example, the parietal or frontal bone may be 10 to 20 millimeters thick, wherein the present invention would work properly with both bone thicknesses, as well as smaller or larger thicknesses.

Other variations of the disclosed fastener are possible. The relative positions of the cap and base can be reversed, for example, by disposing the cap 150 on the interior surface of the cranium and bone plate 18 while the base 100 is disposed along the external surfaces thereof by simply threading the collar 110 of the base 100 and leaving the collar 158 of the cap 150 unthreaded. The cap 150 and base 100 may assume many shapes other than circular, and may, for example, be square or triangular. Bone plates other than in the skull may be secured to surrounding bone, for example, a relatively flat top bone such as the trapezium, mandible, maxilla or bones of the orbit. The outer face of the cap 150 may also be flat, particularly in areas of the skull, such as the temporal bone, with relatively flat external surfaces. The fastener may also be used to fix adjacent members together, even where the members are curved. A malleable material may be used to accommodate differing surface shapes. Such materials include LACTOSORB® copolymer, VHMN polyethylene, polyethyl ketone, silicone, nylon, etc.

Figure 14:
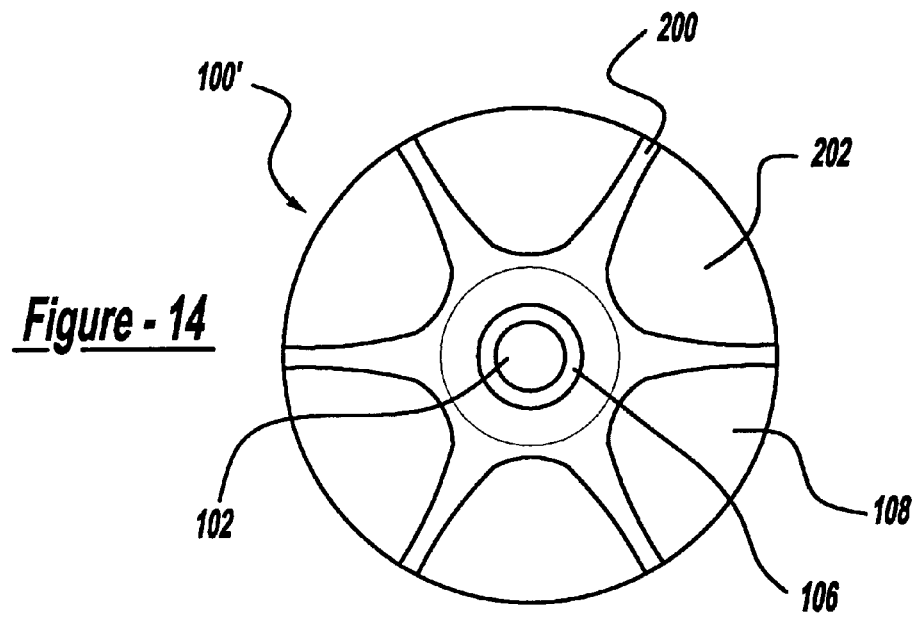
FIG. 14 is a top view of an alternative embodiment of the clamp according to the invention.

In one embodiment, the base and cap may include flexible struts 200 to provide more flexibility than a solid member, as shown in FIG. 14 for exemplary base 100'. The struts 200 are preferably made of a high-density polyethylene. In the disclosed embodiment, each strut 200 does not occupy more than about a 20 to 30 degree sector of the base or cap. The struts 200 radiate from the center of the cap or base to a peripheral ring, but they can alternatively taper, flair, or assume other shapes that sufficiently reduce the solid areas of the base and cap to increase the flexibility such that it conforms to the curvature of the skull when the clamp is tightened to such an extent that the bone in the skull is not fractured or damages. For example, the modulus of flexibility of the cap or base, or each individual strut, is 300,000 to 700,000 PSI.

Figure 15:
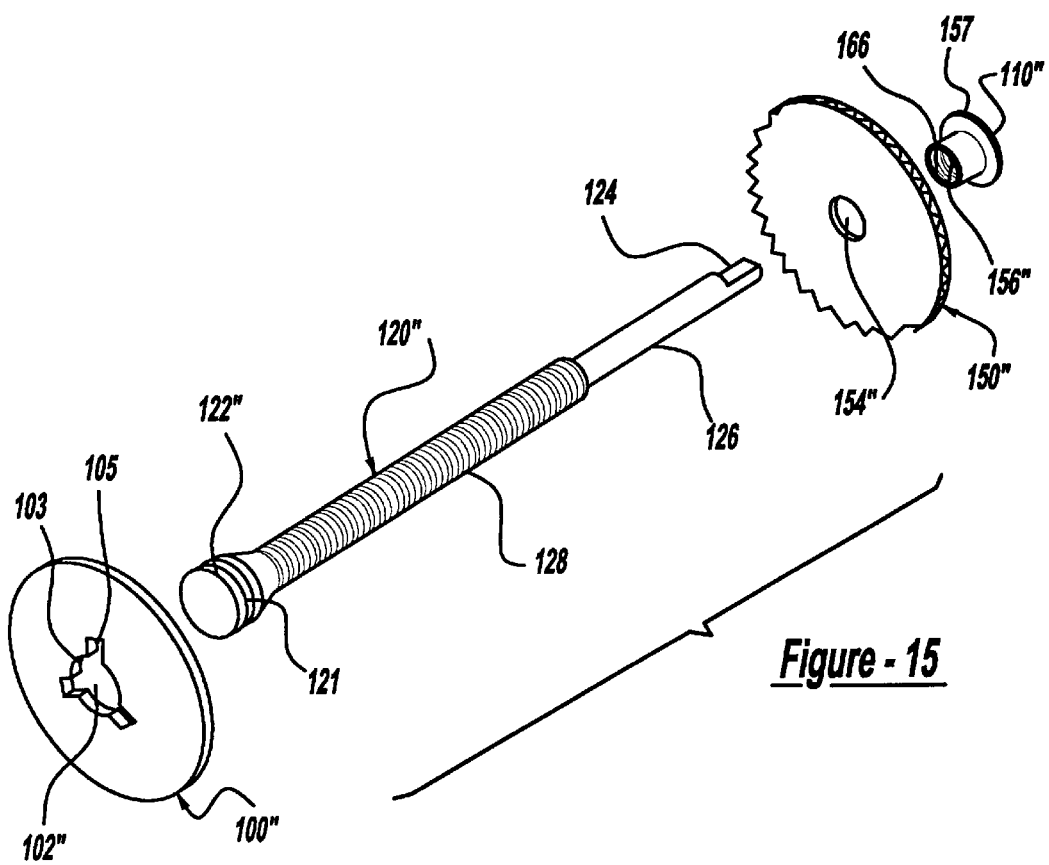
FIG. 15 is an exploded perspective view with an alternative embodiment of the clamp according to the invention.
Figure 16:
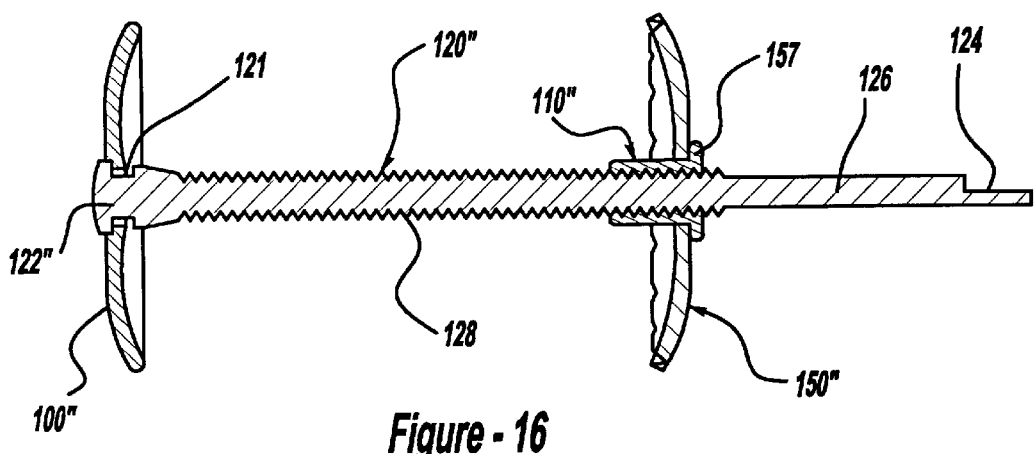
FIG. 16 is a sectional side view of the assembled clamp of FIG. 15.
Figure 17:
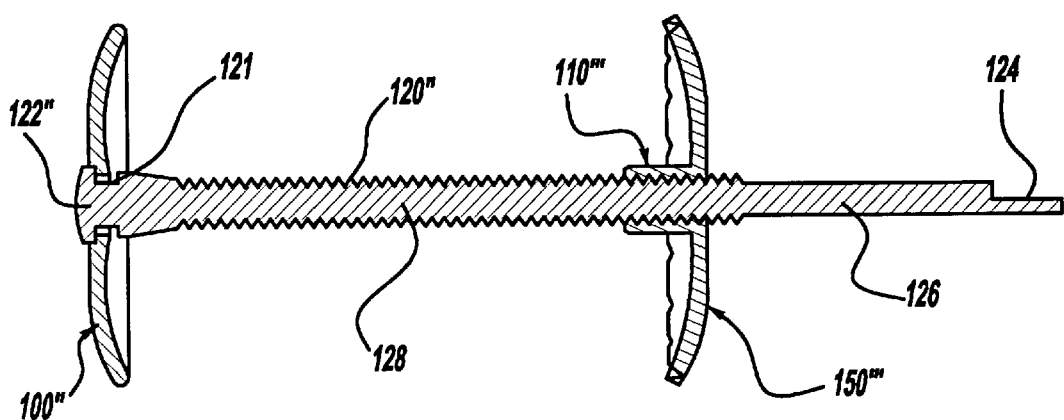
FIG. 17 is a sectional side view of an assembled clamp according to another embodiment of the invention.

In yet another embodiment shown in FIGS. 15–17, the clamp 10 includes a first member or base 100" selectively connected to a second member or cap 150" via a post 120". As before, the cap 150" and base 100" are brought toward one another by an instrument or applier 170. The base 100" is formed by a generally solid disk having a central aperture 102" for rotatably receiving the post 120". Similar reference numbers are used in this description to note features similar to those described for the prior embodiments.

The post 120" includes a head 122" at a first end and a key 124 at a second end. A substantially cylindrical elongated body 126 extends between the head 122" and the key 124, and generally includes ribs or threads 128 along its length. As before, threads 128 are used in the description, but ribs are within the scope of the invention. The head 122" of the post 120" includes a channel 121 for receiving a periphery 103 of the aperture 102" in order to rotatably secure the base 100" to the post 120". Slots 105 allow deflection of the base 100" at the periphery 103 to facilitate insertion of the head 122" in the aperture 102", whereby the periphery 103 is received in the channel 121. In this manner, as described in prior embodiments, the post 120" is able to rotate relative the base 100".

The cap 150" is a generally solid disk having a central aperture disposed coaxially therethrough for receiving the collar 110". The collar 110" includes a central aperture 156" extending therethrough and including internal threads 166 that mate with the threads 128 on the post 120". The collar 110" includes a flange 157 to prevent pulling the collar 110" through the cap 150" during assembly or use. The collar 110" is press fit into the aperture 159 of the cap 150", whereby the collar 110" and cap 150" rotate together. Alternatively, the collar 110" and cap 150" could be threaded together where the threaded engagement between the collar 110" and cap 150" is an opposite thread to that of the engagement between the internal thread 166 of the collar 110" and the thread 128 of the post 120".

In a variation of this latter embodiment, the collar 110" can be a collar 110'" that is formed integral with a cap 150"', as shown in FIG. 17. The operation and use of this variation of the invention is similar to that described for the previous embodiment of the invention, and the inventions shown in FIGS. 15–17 are used and assembled in manners similar to that described above for the prior embodiments.

As used in this specification, conformance to a curved member does not require identical curvature of the conforming member at the surface to which it conforms. Substantial conformity of the members is all that is required, and that includes surfaces between flat planes and curves that precisely conforms to the curved member against which the conforming member seats.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A clamp assembly for repairing a bone defect in a cranium and operable to fix a bone plate relative the surrounding cranium, each of the bone plate and surrounding cranium having a near face and a far face, the clamp assembly comprising:
   a cap;
   a base opposing the cap;
   a post having an elongate body rotatably attached to the base and extending through the cap, the post engaging the cap and base to fasten the cap and base relative one another; and
   an applier operable to rotate the post to position the cap relative to the base in a fastening position on the adjacent bone plate and surrounding cranium, and the applier being removable from the post while leaving the cap and base interconnected.

2. The clamp assembly of claim 1, wherein the post includes external threads.

3. The clamp assembly of claim 2, wherein the cap includes an internally threaded collar for mating engagement with the threads of the post.

4. The clamp assembly of claim 1, wherein the post includes external ribs.

5. The clamp assembly of claim 4, wherein the cap includes a collar adapted for ratcheting engagement with the post to allow the cap to be secured by ratcheting the cap along the threads on the post.

6. The clamp assembly of claim 1, wherein the applier further includes a body having a keyed bore, and the post further includes a key for engaging the keyed bore of the applier.

7. The clamp assembly of claim 1, wherein the cap and base have opposing inner faces that face each other when assembled in use, and the cap further includes teeth extending from the inner face to inhibit rotation of the cap relative to the adjacent members.

8. The clamp assembly of claim 1, wherein the post further includes a torque-limiting feature, wherein the torque-limiting feature prevents over tightening of the cap relative to the base when in the fastening position.

9. The clamp assembly of claim 8, wherein the post further includes a key disposed at a distal end of the elongate body, the key operable to matingly engage the applier, and the torque-limiting feature being disposed at a junction between the elongate body and the key.

10. The clamp assembly of claim 1, wherein at least one of the cap, base and post include resorbable material.

11. The clamp assembly of claim 10, wherein the cap, base and post include resorbable material.

12. The clamp assembly of claim 1, wherein at least one of the cap, base and post include non-resorbable, biocompatible material.

13. The clamp assembly of claim 12, wherein the cap, base and post include non-resorbable, biocompatible material.

14. The clamp assembly of claim 12, wherein the non-resorbable, biocompatible material is titanium.

15. A clamp assembly for repairing a bone defect in a cranium and operable to fix a bone plate relative the surrounding cranium, each of the bone plate and surrounding cranium having a near face and a far face, the clamp assembly comprising:
   a base;
   a cap having an internally threaded collar formed therethrough;
   an externally threaded elongate post rotatably attached to the base and extending through the collar in said cap;
   an applier operable to rotate the post to position the cap relative to the base in a fastening position on the adjacent bone plate and surrounding cranium, and the applier being removable from the post while leaving the cap and base interconnected; and
   wherein the internally threaded collar of the cap engages the externally threaded post to position the cap and base in a fastening position.

16. The clamp assembly of claim 15, wherein the applier further includes a body having a keyed bore, and the post further includes a key for engaging the keyed bore of the applier.

17. The clamp assembly of claim 15, wherein the cap and base have opposing inner faces that face each other when assembled in use, and the cap further includes teeth extending from the inner face to inhibit rotation of the cap relative to the adjacent members.

18. The clamp assembly of claim 15, wherein the post further includes a torque-limiting feature, wherein the torque-limiting feature prevents over tightening of the cap relative to the base when in the fastening position.

19. The clamp assembly of claim 18, wherein the post further includes a key disposed at a distal end of the elongate body, the key operable to matingly engage the applier, and the torque-limiting feature being disposed at a junction between the elongate body and the key.

20. The clamp assembly of claim 15, wherein at least one of the cap, base and post include resorbable material.

21. The clamp assembly of claim 20, wherein the cap, base and post include resorbable material.

22. The clamp assembly of claim 15, wherein at least one of the cap, base and post include non-resorbable, biocompatible material.

23. The clamp assembly of claim 22, wherein the cap, base and post include non-resorbable, biocompatible material.

24. The clamp assembly of claim 22, wherein the non-resorbable, biocompatible material is titanium.

25. A method of fixing a bone plate in a bony defect, wherein the bone plate has opposing internal and external surfaces that are to be held in position substantially co-planar with internal and external surfaces of surrounding bone, and a transverse face of the bone plate is to be fixed in apposition against a transverse face of the surrounding bone along a border of junction between the bone plate and surrounding bone, the method comprising:
   rotatably connecting an elongated externally threaded post to a base;
   extending the post through a cap to engage the threaded post with the cap;
   positioning the base and cap on opposing internal and external surfaces of the bone plate, with a portion of each of the base and cap overlapping the border of junction; and rotating an applier to cause the post to rotate in the base and position the cap and base in a fastening position wherein the base and cap are in tight engagement against the opposing internal and external surfaces of the bone plate.

26. The method of claim 25, further comprising removing a distal end of the post projecting from the cap and leaving a proximal portion of the post projecting from the cap.

27. The method of claim 25, further comprising deforming the proximal portion of the post projecting from the cap secure the base and cap in the fastening positioning.

28. The method of claim 25, further comprising assembling the base, post, cap and applier prior to the step of rotating the applier.

29. The method of claim 25, further comprising removing the applier.

* * * * *